(12) United States Patent
Tomiha et al.

(10) Patent No.: US 11,360,170 B2
(45) Date of Patent: Jun. 14, 2022

(54) MAGNETIC RESONANCE IMAGING APPARATUS

(71) Applicant: CANON MEDICAL SYSTEMS CORPORATION, Otawara (JP)

(72) Inventors: Sadanori Tomiha, Nasushiobara (JP); Masao Yui, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 0 days.

(21) Appl. No.: 17/089,081

(22) Filed: Nov. 4, 2020

(65) Prior Publication Data

US 2021/0132166 A1 May 6, 2021

(30) Foreign Application Priority Data

Nov. 6, 2019 (JP) .............................. JP2019-201228

(51) Int. Cl.
*G01R 33/36* (2006.01)
*A61B 5/055* (2006.01)
*G01R 33/54* (2006.01)
*G01R 33/56* (2006.01)

(52) U.S. Cl.
CPC .......... *G01R 33/3635* (2013.01); *A61B 5/055* (2013.01); *G01R 33/543* (2013.01); *G01R 33/5608* (2013.01)

(58) Field of Classification Search
CPC .............. G01R 33/3635; G01R 33/543; G01R 33/5608; A61B 5/055
See application file for complete search history.

(56) References Cited

U.S. PATENT DOCUMENTS

| 6,222,365 | B1 | 4/2001 | Taniguchi et al. |
| 7,759,938 | B2* | 7/2010 | Prado ..................... G01N 24/08 324/319 |
| 2003/0220559 | A1 | 11/2003 | Ehnholm et al. |

(Continued)

FOREIGN PATENT DOCUMENTS

| JP | 63-257536 A | 10/1988 |
| JP | 04-026410 A | 1/1992 |

(Continued)

*Primary Examiner* — Gregory H Curran
(74) *Attorney, Agent, or Firm* — Oblon, McClelland, Maier & Neustadt, L.L.P.

(57) ABSTRACT

A magnetic resonance imaging apparatus according to an embodiment includes a static magnetic field generator, a transmit/receive system, and an acquiring means. The static magnetic field generator is configured to apply a second static magnetic field in addition to a first static magnetic field serving as a reference. The transmit/receive system is configured to perform transmitting and receiving at a single frequency. The processing circuitry is configured to acquire a magnetic resonance signal by employing the transmit/receive system. The transmit/receive system is configured to perform transmitting and receiving at a resonance frequency of a hydrogen nucleus in a state in which the first static magnetic field is applied and is configured to perform transmitting and receiving at a resonance frequency of a nuclide different from the hydrogen nucleus in a state in which the second static magnetic field is applied in addition to the first static magnetic field.

9 Claims, 4 Drawing Sheets

(56) References Cited

U.S. PATENT DOCUMENTS

| | | | |
|---|---|---|---|
| 2005/0240098 A1 | 10/2005 | Zhong et al. | |
| 2010/0148773 A1 | 6/2010 | Chen et al. | |
| 2011/0254550 A1 | 10/2011 | Chen et al. | |
| 2016/0299204 A1* | 10/2016 | Cousin | G01R 33/4616 |
| 2019/0072627 A1* | 3/2019 | Stainsby | G01R 33/38 |

FOREIGN PATENT DOCUMENTS

| | | |
|---|---|---|
| JP | 04-102442 A | 4/1992 |
| JP | 2000-237164 A | 9/2000 |
| JP | 2009-297257 A | 12/2009 |
| JP | 2010-184115 A | 8/2010 |
| JP | 2011-083413 A | 4/2011 |

* cited by examiner

MAGNETIC RESONANCE IMAGING APPARATUS

CROSS-REFERENCE TO RELATED APPLICATIONS

This application is based upon and claims the benefit of priority from Japanese Patent Application No. 2019-201228, filed on Nov. 6, 2019; the entire contents of which are incorporated herein by reference.

FIELD

Embodiments described herein relate generally to a magnetic resonance imaging apparatus.

BACKGROUND

Magnetic Resonance Imaging (MRI) apparatuses are apparatuses configured to render, in images, chemical and physical microscopic information of substances, by using a magnetic resonance phenomenon. In this situation, the magnetic resonance phenomenon is a phenomenon in which, when an aggregation of spins of a targeted atomic nucleus is placed in a static magnetic field, the atomic nucleus resonates with a radio frequency magnetic field rotating at a specific frequency (hereinafter, "resonance frequency") corresponding to magnetic moment unique to the atomic nucleus and to the intensity of the static magnetic field and emits a signal in a relaxation process.

Such MRI apparatuses are, generally speaking, configured to perform an imaging process while targeting hydrogen nuclei (protons)$^1$H; however, other techniques are also known by which an imaging process is performed while targeting a nuclide different from $^1$H.

DETAILED DESCRIPTION

An MRI apparatus according to an embodiment includes a static magnetic field generator, a transmit/receive system, and an acquiring means. The static magnetic field generator is configured to apply a second static magnetic field in addition to a first static magnetic field serving as a reference. The transmit/receive system is configured to perform transmitting and receiving at a single frequency. The acquiring means is configured to acquire a magnetic resonance signal by employing the transmit/receive system. The transmit/receive system is configured to perform transmitting and receiving at a resonance frequency of a hydrogen nucleus in a state in which the first static magnetic field is applied and is configured to perform transmitting and receiving at a resonance frequency of a nuclide different from the hydrogen nucleus in a state in which the second static magnetic field is applied in addition to the first static magnetic field.

Exemplary embodiments of an MRI apparatus of the present disclosure will be explained in detail below, with reference to the accompanying drawings.

First Embodiment

Figure 1:
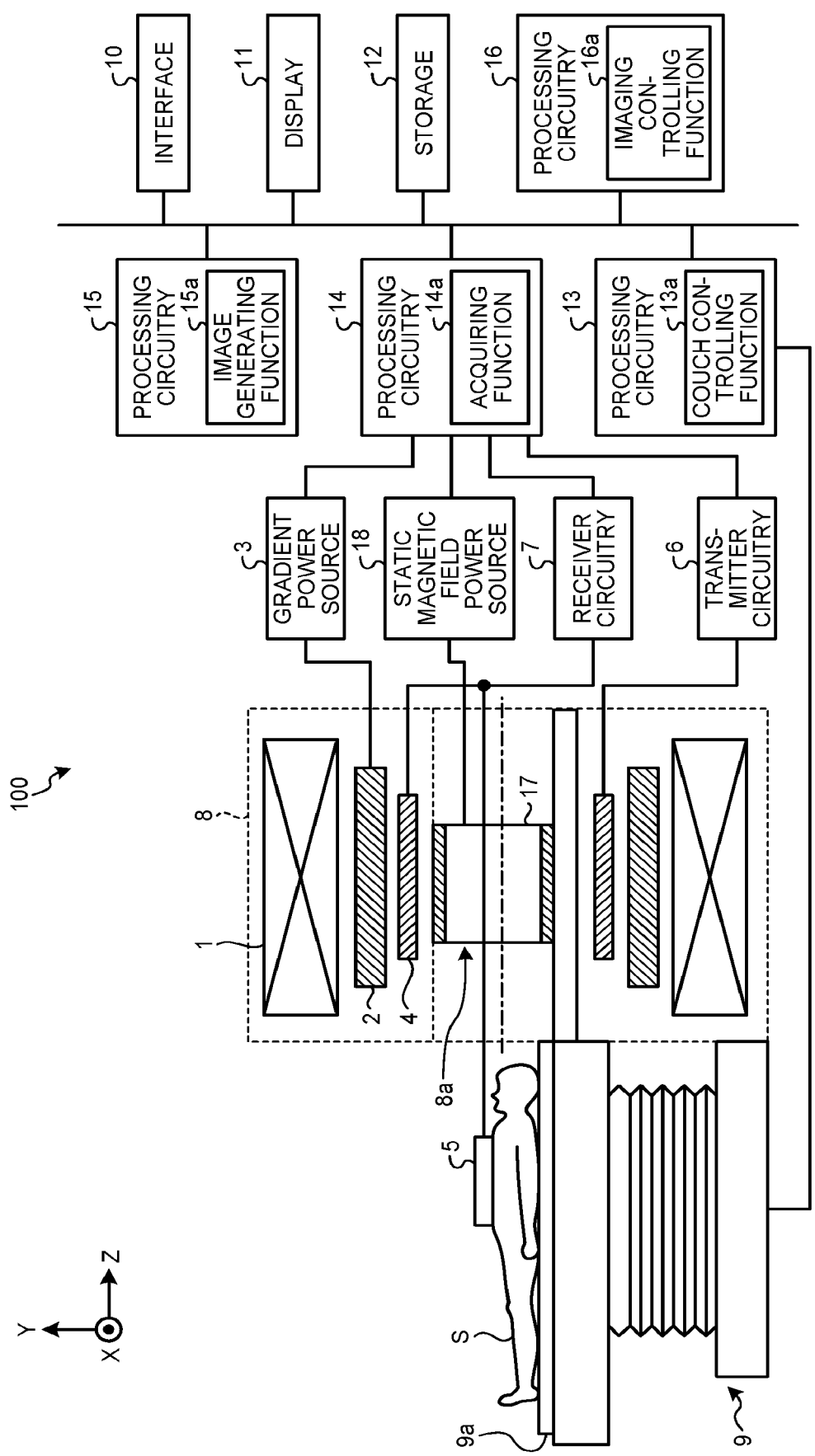
FIG. 1 is a diagram illustrating an exemplary configuration of an MRI apparatus according to a first embodiment.

FIG. 1 is a diagram illustrating an exemplary configuration of an MRI apparatus according to a first embodiment.

For example, as illustrated in FIG. 1, an MRI apparatus 100 according to the present embodiment includes a first static magnetic field magnet 1, a gradient coil 2, a gradient power source 3, a whole body Radio Frequency (RF) coil 4, a local RF coil 5, transmitter circuitry 6, receiver circuitry 7, a gantry 8, a couch 9, an interface 10, a display 11, a storage 12, pieces of processing circuitry 13 to 16, a second static magnetic field magnet 17, and a static magnetic field power source 18.

The first static magnetic field magnet 1 is configured to generate a static magnetic field in an image taking space in which an examined subject S is placed. More specifically, the first static magnetic field magnet 1 is formed to have a hollow and substantially circular cylindrical shape (which may have an oval cross-section orthogonal to the central axis thereof) and is configured to generate a static magnetic field in the image taking space formed on the inner circumferential side thereof. For example, the first static magnetic field magnet 1 is a super conductive magnet or a permanent magnet.

The gradient coil 2 is arranged on the inside of the first static magnetic field magnet 1 and is configured to generate gradient magnetic fields in the image taking space in which the subject S is placed. More specifically, the gradient coil 2 is formed to have a hollow and substantially circular cylindrical shape (which may have an oval cross-section orthogonal to the central axis thereof) and includes an X-coil, a Y-coil, and a Z-coil corresponding to an X-axis, a Y-axis, and a Z-axis that are orthogonal to one another. Each of the X-, Y-, and Z-coils is configured to generate, in the image taking space, a gradient magnetic field that linearly changes along the corresponding axial direction, on the basis of an electric current supplied thereto from the gradient power source 3. In this situation, the Z-axis is set so as to extend along a magnetic flux of the static magnetic field generated by the first static magnetic field magnet 1. The X-axis is set so as to extend along the horizontal direction orthogonal to the Z-axis. The Y-axis is set so as to extend along the vertical direction orthogonal to the Z-axis. As a result, the X-axis, the Y-axis, and the Z-axis structure an apparatus coordinate system unique to the MRI apparatus 100.

The gradient power source 3 is configured to cause the gradient magnetic fields to be generated in the image taking space, by supplying the electric current to the gradient coil 2. More specifically, by individually supplying the electric current to each of the X-, Y-, and Z-coils included in the gradient coil 2, the gradient power source 3 is configured to cause the gradient magnetic fields to be generated in the image taking space, the gradient magnetic fields linearly changing along a readout direction, a phase encode direction, and a slice direction, respectively, that are orthogonal to one another. In the following sections, the gradient magnetic field along the readout direction will be referred to as a readout gradient magnetic field. The gradient magnetic field along the phase encode direction will be referred to as a phase encode gradient magnetic field. The gradient magnetic field along the slice direction will be referred to as a slice gradient magnetic field.

In this situation, as each being superimposed on the static magnetic field generated by the first static magnetic field magnet 1, the readout gradient magnetic field, the phase encode gradient magnetic field, and the slice gradient magnetic field append spatial position information to a magnetic resonance signal emitted from the subject S. More specifically, the readout gradient magnetic field appends position information along the readout direction to the magnetic resonance signal, by changing the frequency of the magnetic resonance signal in accordance with the position in the readout direction. Further, the phase encode gradient magnetic field appends position information along the phase encode direction to the magnetic resonance signal, by changing the phase of the magnetic resonance signal along the phase encode direction. Further, the slice gradient magnetic field appends position information along the slice direction to the magnetic resonance signal. For example, when imaged regions are slice regions (two-dimensional [2D] imaging), the slice gradient magnetic field is used for determining the orientations, the thicknesses, and the quantity of the slice regions. When an imaged region is a volume region (three-dimensional [3D] imaging), the slice gradient magnetic field is used for changing the phase of the magnetic resonance signal in accordance with the position in the slice direction. Accordingly, the axis along the readout direction, the axis along the phase encode direction, and the axis along the slice direction structure a logical coordinate system for defining the slice regions or the volume region to be imaged.

The whole body RF coil 4 is arranged on the inner circumferential side of the gradient coil 2 and is configured to transmit a radio frequency magnetic field to the subject S placed in the image taking space and to receive the magnetic resonance signal emitted from the subject S due to an influence of the radio frequency magnetic field. More specifically, the whole body RF coil 4 is formed to have a hollow and substantially circular cylindrical shape (which may have an oval cross-section orthogonal to the central axis thereof) and is configured to transmit the radio frequency magnetic field to the subject S placed in the image taking space positioned on the inner circumferential side thereof, on the basis of a radio frequency pulse signal supplied thereto from the transmitter circuitry 6. Further, the whole body RF coil 4 is configured to receive the magnetic resonance signal emitted from the subject S due to the influence of the radio frequency magnetic field and to output the received magnetic resonance signal to the receiver circuitry 7.

The local RF coil 5 is configured to receive the magnetic resonance signal emitted from the subject S. More specifically, a plurality of types of local RF coils 5 are prepared so as to be applied to different sites of the subject S. When an imaging process is performed on the subject S, the local RF coil 5 is arranged in the vicinity of the surface of the site to be imaged. Further, the local RF coil 5 is configured to receive the magnetic resonance signal emitted from the subject S due to the influence of the radio frequency magnetic field transmitted by the whole body RF coil 4 and to output the received magnetic resonance signal to the receiver circuitry 7. In this situation, the local RF coil 5 may further have a function of transmitting a radio frequency magnetic field to the subject S. In that situation, the local RF coil 5 is connected to the transmitter circuitry 6 and is configured to transmit the radio frequency magnetic field to the subject S, on the basis of a radio frequency pulse signal supplied thereto from the transmitter circuitry 6. For example, the local RF coil 5 may be a surface coil or a phased array coil structured by combining together a plurality of surface coils as the elements thereof.

The transmitter circuitry 6 is configured to output the radio frequency pulse signal corresponding to a resonance frequency (which may be referred to as a Larmor frequency) unique to targeted atomic nuclei placed in the static magnetic field, to the whole body RF coil 4. More specifically, the transmitter circuitry 6 includes a pulse generator, a radio frequency generator, a modulator, and an amplifier. The pulse generator is configured to generate a waveform of the radio frequency pulse signal. The radio frequency generator is configured to generate a radio frequency signal having the resonance frequency. The modulator is configured to generate the radio frequency pulse signal by modulating the amplitude of the radio frequency signal generated by the radio frequency generator, with the waveform generated by the pulse generator. The amplifier is configured to amplify the radio frequency pulse signal generated by the modulator and to output the amplified signal to the whole body RF coil 4.

The receiver circuitry 7 is configured to generate magnetic resonance data on the basis of the magnetic resonance signal output from the whole body RF coil 4 or the local RF coil 5 and to output the generated magnetic resonance data to the processing circuitry 14. For example, the receiver circuitry 7 includes a selector, a pre-amplifier, a phase detector, and an Analog/Digital (A/D) converter. The selector is configured to selectively receive an input of the magnetic resonance signal output from the whole body RF coil 4 or the local RF coil 5. The pre-amplifier is configured to power-amplify the magnetic resonance signal output from the selector. The phase detector is configured to detect the phase of the magnetic resonance signal output from the pre-amplifier. The A/D converter is configured to generate the magnetic resonance data by converting an analog signal output from the phase detector into a digital signal and to output the generated magnetic resonance data to the processing circuitry 14. In this situation, the processes described as being performed by the receiver circuitry 7 do not all necessarily have to be performed by the receiver circuitry 7. One or more of the processes (e.g., the process by the A/D converter) may be performed by the whole body RF coil 4 or the local RF coil 5.

The gantry 8 has a bore 8a formed to have a hollow and substantially circular cylindrical shape (which may have an oval cross-section orthogonal to the central axis thereof) and houses therein the first static magnetic field magnet 1, the gradient coil 2, and the whole body RF coil 4. More specifically, the gantry 8 houses therein the first static magnetic field magnet 1, the gradient coil 2, and the whole body RF coil 4, while the whole body RF coil 4 is arranged on the outer circumferential side of the bore 8a; the gradient coil 2 is arranged on the outer circumferential side of the whole body RF coil 4; and the first static magnetic field magnet 1 is arranged on the outer circumferential side of the gradient coil 2. In this situation, the space inside the bore 8a of the gantry 8 serves as the image taking space in which the subject S is placed at the time of an imaging process.

The couch 9 includes a couchtop 9a on which the subject S is placed and a moving mechanisms configured to move the couchtop 9a in up-and-down directions and horizontal directions. In this situation, the up-and-down directions are vertical directions, whereas the horizontal directions are the directions along the central axis of the first static magnetic field magnet 1. Because the couch 9 is configured in this manner, it is possible to change the height of the couchtop 9a by moving the couchtop 9a in the up-and-down directions. Further, the couch 9 is configured so that, by moving the couchtop 9a in the horizontal directions, it is possible to change the position of the couchtop 9a between the space outside of the gantry 8 and the image taking space formed in the bore 8a inside the gantry 8.

The interface 10 is configured to receive operations to input various types of instructions and various type of information from an operator. More specifically, the interface 10 is connected to the processing circuitry 16 and is configured to convert the input operations received from the operator into electrical signals and to output the electrical signals to the processing circuitry 16. For example, the interface 10 is realized by using a trackball, a switch button, a mouse, a keyboard, a touch-pad on which input operations can be performed by touching an operation surface thereof, a touch-screen in which a display screen and a touch-pad are integrally formed, contactless input circuitry using an optical sensor, audio input circuitry, and/or the like, that are used for setting image taking conditions, a Region of Interest (ROI), and the like. In the present disclosure, the interface 10 does not necessarily have to include one or more physical operation component parts such as a mouse, a keyboard, and/or the like. For instance, possible examples of the interface 10 include electrical signal processing circuitry configured to receive an electrical signal corresponding to an input operation from an external input device provided separately from the apparatus and to output the electrical signal to controlling circuitry.

The display 11 is configured to display various types of information and various types of images. More specifically, the display 11 is connected to the processing circuitry 16 and is configured to convert data of the various types of information and the various types of images sent thereto from the processing circuitry 16 into display-purpose electrical signals and to output the display-purpose electrical signals. For example, the display 11 is realized by using a liquid crystal monitor, a Cathode Ray Tube (CRT) monitor, a touch panel, or the like.

The storage 12 is configured to store therein various types of data. More specifically, the storage 12 is configured to store therein magnetic resonance data and image data. For example, the storage 12 is realized by using a semiconductor memory element such as a Random Access Memory (RAM) or a flash memory, or a hard disk, an optical disk, or the like.

The processing circuitry 13 includes a couch controlling function 13a. The couch controlling function 13a is configured to control operations of the couch 9, by outputting a control-purpose electrical signal to the couch 9. For example, the couch controlling function 13a is configured to receive, from the operator, an instruction to move the couchtop 9a in an up-and-down direction or a horizontal direction via the interface 10 or an operation panel provided for the gantry 8 and to bring the moving mechanism included in the couch 9 into operation so as to move the couchtop 9a according to the received instruction. For example, when an imaging process is performed on the subject S, the couch controlling function 13a is configured to move the couchtop 9a on which the subject S is placed into the image taking space formed in the bore 8a inside the gantry 8.

The processing circuitry 14 includes an acquiring function 14a. The acquiring function 14a is configured to acquire magnetic resonance data of the subject S by executing various types of pulse sequences. More specifically, the acquiring function 14a is configured to execute the various types of pulse sequences by driving the gradient power source 3, the transmitter circuitry 6, and the receiver circuitry 7, according to sequence execution data output from the processing circuitry 16. In this situation, the sequence execution data is data representing the pulse sequences and is information defining: the timing with which the electric current is to be supplied from the gradient power source 3 to the gradient coil 2 and the intensity of the electric current to be supplied; the timing with which the radio frequency pulse signal is to be supplied by the transmitter circuitry 6 to the whole body RF coil 4 and the intensity of the radio frequency pulse to be supplied; the timing with which the magnetic resonance signal is to be sampled by the receiver circuitry 7, and the like. Further, the acquiring function 14a is configured to receive the magnetic resonance data output from the receiver circuitry 7 as a result of executing the pulse sequences and to store the received magnetic resonance data into the storage 12. In this situation, the magnetic resonance data stored in the storage 12 is stored as data representing a two- or three-dimensional k-space, as a result of the position information along the directions of the readout direction, the phase out direction, and the slice direction being appended by the readout gradient magnetic field, the phase encode gradient magnetic field, and the slice gradient magnetic field described above.

The processing circuitry 15 includes an image generating function 15a. The image generating function 15a is configured to generate various types of images on the basis of the magnetic resonance data acquired by the processing circuitry 14. More specifically, the image generating function 15a is configured to generate a two- or three-dimensional image by reading the magnetic resonance data acquired by the processing circuitry 14 from the storage 12 and performing a reconstructing process such as a Fourier transform on the read magnetic resonance data. After that, the image generating function 15a is configured to store the generated image into the storage 12.

The processing circuitry 16 includes an imaging controlling function 16a. The imaging controlling function 16a is configured to control the entirety of the MRI apparatus 100 by controlling the constituent elements of the MRI apparatus 100. More specifically, the imaging controlling function 16a is configured to cause the display 11 to display a Graphical User Interface (GUI) used for receiving operations to input various types of instructions and various types of information from the operator and is configured to control the constituent elements of the MRI apparatus 100 in accordance with input operations received via the interface 10. For example, the imaging controlling function 16a is configured to cause the magnetic resonance data to be acquired by generating the sequence execution data on the basis of the image taking conditions input by the operator and outputting the generated sequence execution data to the processing circuitry 14. Further, for example, by controlling the processing circuitry 15, the imaging controlling function 16a is configured to cause images to be generated on the basis of the magnetic resonance data acquired by the processing circuitry 14. Also, for example, the imaging controlling function 16a is configured to read any of the images stored in the storage 12 in response to a request from the operator and is configured to cause the display 11 to display the read image.

In this situation, the pieces of processing circuitry described above are realized, for example, by using one or more processors. In that situation, the processing functions of the pieces of processing circuitry are, for example, stored in the storage 12, in the form of computer-executable programs. Further, the pieces of processing circuitry realize the processing functions corresponding to the programs, by reading and executing the programs from the storage 12. In other words, the pieces of processing circuitry that have read the programs have the functions illustrated within the pieces of processing circuitry in FIG. 1.

The present example is explained on the assumption that each of the processors is realized by using a single processor; however, possible embodiments are not limited to this example. For instance, another arrangement is also acceptable in which each of the pieces of processing circuitry is structured by combining together a plurality of independent processors, so that each of the processing functions is realized as a result of the processors executing the program. Further, the processing functions of the pieces of processing circuitry may be realized as being distributed among, or integrated into, one or more pieces of processing circuitry. Furthermore, although the example illustrated in FIG. 1 indicates that the single storage (i.e., the storage 12) stores therein the programs corresponding to the processing functions, it is also acceptable to arrange a plurality of storages in a distributed manner, so that each of the pieces of processing circuitry reads the corresponding program from a corresponding one of the individual storages.

An overall configuration of the MRI apparatus 100 according to the present embodiment has thus been explained. The MRI apparatus 100 according to the present embodiment structured as described above is capable of performing imaging processes while targeting hydrogen nuclei $^1$H and a nuclide different from $^1$H.

In relation to this, atomic nuclei have different resonance frequencies in correspondence with different nuclides, depending on the magnetic rotation rate that is different for each nucleus. For this reason, when imaging processes are performed while targeting a plurality of nuclides, for example, it is possible to use various methods such as: providing a dedicated transmit/receive system for each nuclide; structuring the transmit/receive system so as to be able to perform transmitting and receiving at multiple resonance frequencies (called "Dual Tune"); setting the band of the transmit/receive system to a wide band; and changing the RF coil for each imaging process so as to use a dedicated RF coil suitable for the targeted nuclide.

However, when these methods are used, the quality of the images acquired from the imaging processes might be degraded in some situations. For example, when a dedicated transmit/receive system is provided for each nuclide, or when the transmit/receive system is structured to be able to perform transmitting and receiving at multiple resonance frequencies, if the configuration targeted only $^1$H, the transmit/receive system would have unnecessary circuitry or elements added thereto. In that situation, because electrical noise would increase, the image quality might be degraded. In another example, when the band of the transmit/receive system is set to a wide band, because a larger amount of noise would be detected in correspondence with the wider band, the image quality might be thereby degraded. In yet another example, when the RF coil is changed for each imaging process so as to use a dedicated RF coil suitable for the targeted nuclide, the subject might move, in some situations, while the RF coil is being changed. In the situation where an evaluation is made by superimposing an image of another nuclide on an image of $^1$H, the image quality of the superimposed images might be degraded due to a positional misalignment between the images.

For these reasons, the MRI apparatus 100 according to the present embodiment is configured to be able to perform imaging processes with high image quality, while targeting $^1$H as well as a nuclide different from $^1$H.

More specifically, the MRI apparatus 100 includes a static magnetic field generator configured to apply a second static magnetic field in addition to a first static magnetic field serving as a reference; a transmit/receive system configured to perform transmitting and receiving at a single frequency; and an acquiring means configured to acquire a magnetic resonance signal by employing the transmit/receive system. Further, the transmit/receive system is configured to perform transmitting and receiving at the resonance frequency of $^1$H in the state in which the first static magnetic field is applied and is configured to perform transmitting and receiving at the resonance frequency of a nuclide different from $^1$H in the state in which the second static magnetic field is applied in addition to the first static magnetic field.

In the present embodiment, the static magnetic field generator is realized by the first static magnetic field magnet 1, the second static magnetic field magnet 17, and the static magnetic field power source 18. Further, the transmit/receive system is realized by the whole body RF coil 4, the local RF coil 5, the transmitter circuitry 6, and the receiver circuitry 7 described above. Further, the acquiring means is realized by the acquiring function 14a included in the processing circuitry 14 described above.

The first static magnetic field magnet 1 is configured to generate, in the image taking space, the first static magnetic field having a predetermined magnitude and serving as a reference.

By using the electric current supplied thereto from the static magnetic field power source 18, the second static magnetic field magnet 17 is configured to generate, in a static magnetic field space, the second static magnetic field having a predetermined magnitude corresponding to the nuclide targeted in the imaging process. More specifically, the second static magnetic field magnet 17 is an electromagnet realized by using a coil formed to have a hollow and substantially circular cylindrical shape, or the like and is provided so as to enclose the magnetic field center of the first static magnetic field.

Under control of the acquiring function 14a, the static magnetic field power source 18 is configured to supply the second static magnetic field magnet 17 with the electric current used for causing the second static magnetic field magnet 17 to generate the second static magnetic field.

The acquiring function 14a is configured to acquire the magnetic resonance signal, by controlling the static magnetic field generator and the transmit/receive system.

More specifically, when $^1$H is targeted in an imaging process, the acquiring function 14a is configured to create the state in which only the first static magnetic field is applied, by controlling the static magnetic field power source 18 so as not to supply the electric current to the second static magnetic field magnet 17. In that situation, the magnitude of the second static magnetic field is zero. In contrast, when a nuclide different from $^1$H is targeted in an imaging process, the acquiring function 14a is configured to create the state in which the second static magnetic field is applied in addition to the first static magnetic field, by controlling the static magnetic field power source 18 so as to supply the electric current to the second static magnetic field magnet 17. In that situation, the magnitude of the second static magnetic field is at the predetermined level corresponding to the nuclide targeted in the imaging process.

Further, the acquiring function 14a is configured to control the transmit/receive system in accordance with the nuclide targeted in the imaging process. As a result of this control, the transmit/receive system performs transmitting and receiving at a first frequency tuned to the resonance frequency of $^1$H. Further, in the state in which the first static magnetic field is applied, the transmit/receive system is configured to perform transmitting and receiving at the first frequency. In contrast, in the state in which the second static magnetic field is applied in addition to the first static magnetic field, the transmit/receive system is configured to perform transmitting and receiving in the state in which the resonance frequency of the nuclide different from $^1$H is tuned to the first frequency by the first static magnetic field and the second static magnetic field.

In this situation, the magnitude of the second static magnetic field and the first frequency are set in accordance with the magnitude of the first static magnetic field and the nuclide targeted in the imaging process. Further, the direction of the second static magnetic field may be the same as the direction of the first static magnetic field or may be the opposite direction. When the direction of the second static magnetic field is configured to be the same as the direction of the first static magnetic field, the magnitude of the static magnetic field applied at the time of an imaging process is larger. When the direction of the second static magnetic field is configured to be opposite of the direction of the first static magnetic field, the magnitude of the static magnetic field applied to the image taking space is smaller.

For example, let us discuss an example in which the magnitude of the first static magnetic field is 1.5 Tesla (T), while the nuclides targeted in the imaging processes are $^1$H and $^{19}$F.

In this situation, in the 1.5-T static magnetic field, the resonance frequency of $^1$H is approximately 64 MHz, whereas the resonance frequency of $^{19}$F is approximately 60 MHz. For this reason, for example, when the frequency of the transmitting and receiving is set at 64 MHz, it is possible to acquire magnetic resonance signals of $^1$H, but is impossible to acquire magnetic resonance signals of $^{19}$F. In contrast, in a 1.6-T static magnetic field, the resonance frequency of $^{19}$F is approximately 64 MHz, which is substantially equal to the resonance frequency of $^1$H in a 1.5-T static magnetic field.

Accordingly, for example, when the magnitude of the first static magnetic field is 1.5 T, while the nuclides targeted in the imaging processes are $^1$H and $^{19}$F, the magnitude of the second static magnetic field shall be set to 0.1 T, and the first frequency shall be set at 64 MHz.

With these arrangements, when an imaging process is performed while targeting $^1$H, the transmit/receive system is able to acquire the magnetic resonance signals of $^1$H by performing the transmitting and receiving at the first frequency in the state in which only the first static magnetic field is applied. In contrast, when an imaging process is performed while targeting $^{19}$F, the transmit/receive system is able to acquire the magnetic resonance signals of $^{19}$F, by performing the transmitting and receiving at the first frequency in the state in which the second static magnetic field is applied in addition to the first static magnetic field.

In other words, by switching between the state in which only the first static magnetic field is applied and the state in which the second static magnetic field is applied in addition to the first static magnetic field, it is possible to acquire the magnetic resonance signals of $^1$H and $^{19}$F, by using the single frequency tuned to the resonance frequency of $^1$H.

As explained above, in the present embodiment, in the state in which the second static magnetic field is applied in addition to the first static magnetic field, the transmit/receive system is configured to perform the transmitting and receiving in the state in which the resonance frequency of the nuclide different from $^1$H is tuned to the first frequency by the first static magnetic field and the second static magnetic field.

In this situation, the state in which the resonance frequency of the nuclide different from $^1$H is tuned to the first frequency denotes the state in which the resonance frequency of the nuclide is tuned so as to be included in the band of the transmit/receive system and the band of the image.

For example, the resonance frequency of the nuclide different from $^1$H is tuned so as to be included in the narrowest band among the bands of the whole body RF coil 4, the local RF coil 5, the transmitter circuitry 6, the receiver circuitry 7, and the image.

Further, when the nuclide different from $^1$H targeted in the imaging process is a nuclide of which the spin rotation direction is opposite to that of $^1$H, the transmit/receive system is configured to tune the resonance frequency of the nuclide different from $^1$H to the first frequency, by inverting the phase of the radio frequency used in the transmitting and receiving in the state in which the second static magnetic field is applied in addition to the first static magnetic field.

For example, when the whole body RF coil 4 is a Quadrature Detection (QD) coil configured to generate a radio frequency magnetic field by receiving, from two power supply points, inputs of radio frequency currents of which the phases are different by 90 degrees from each other, the transmit/receive system is configured to tune the resonance frequency of the nuclide different from $^1$H to the first frequency, by inverting the phase (IQ) of the radio frequency current supplied to the whole body RF coil 4.

With these arrangements, for example, it is possible to perform imaging processes while targeting a nuclide (e.g., $^3$He, 129Xe, etc.) of which the spin rotation direction is opposite to that of $^1$H.

Further, in the state in which the second static magnetic field is applied in addition to the first static magnetic field, the transmit/receive system is configured to set the receive gain of the magnetic resonance signals of the nuclide different from $^1$H, to be larger than the receive gain of the magnetic resonance signals of $^1$H.

Normally, magnetic resonance signals emitted from nuclides other than $^1$H are smaller in magnitude than magnetic resonance signals emitted from $^1$H. However, as a result of adjusting the receive gain as described above, it is possible to improve the image quality when imaging processes are performed while targeting a nuclide different from $^1$H.

Figure 2:
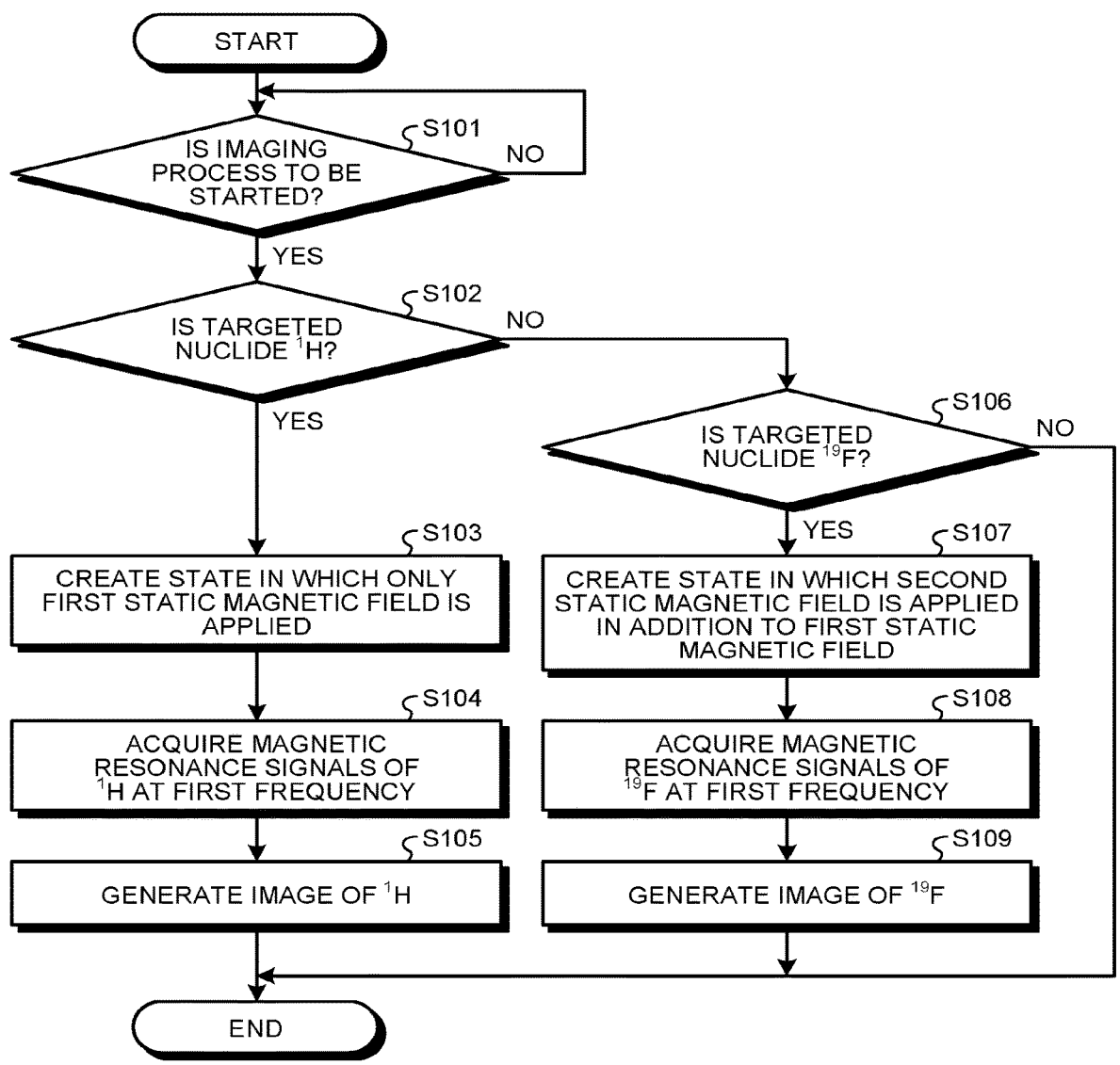
FIG. 2 is a flowchart illustrating a flow in an imaging process performed by the MRI apparatus according to the first embodiment.

FIG. 2 is a flowchart illustrating a flow in an imaging process performed by the MRI apparatus according to the first embodiment.

Similarly to the above example, in the present example, the magnitude of the first static magnetic field is 1.5 T, while the nuclides targeted in the imaging processes are $^1$H and $^{19}$F. It is assumed that the magnitude of the second static magnetic field is set to 0.1 T, while the first frequency is set at 64 MHz.

For example, as illustrated in FIG. 2, in the present embodiment, the imaging controlling function 16a receives an instruction to start an imaging process from the operator (step S101: Yes). In this situation, for example, the imaging controlling function 16a also receives a designation of a nuclide targeted in the imaging process, as one of the image taking conditions, in addition to receiving the instruction to start the imaging process.

In this situation, when the targeted nuclide is $^1$H (step S102: Yes), the acquiring function 14a creates a state in which only the first static magnetic field is applied, by controlling the static magnetic field power source 18 so as not to supply an electric current to the second static magnetic field magnet 17 (step S103).

Subsequently, the acquiring function 14*a* acquires magnetic resonance signals of $^1$H, by controlling the transmit/receive system so as to perform transmitting and receiving at the first frequency (step S104). After that, the image generating function 15*a* generates an image of $^1$H, on the basis of acquired magnetic resonance signals (step S105).

In contrast, when the targeted nuclide is $^{19}$F (step S102: No; and step S106: Yes), the acquiring function 14*a* creates a state in which the second static magnetic field is applied in addition to the first static magnetic field, by controlling the static magnetic field power source 18 so as to supply an electric current to the second static magnetic field magnet 17 (step S107).

Subsequently, by controlling the transmit/receive system so as to perform transmitting and receiving at the first frequency, the acquiring function 14*a* acquires magnetic resonance signals of $^{19}$F (step S108). After that, the image generating function 15*a* generates an image of $^{19}$F, on the basis of the acquired magnetic resonance signals (step S109).

When the targeted nuclide designated by the operator is neither $^1$H nor $^{19}$F (step S102: No; and step S106: No), the acquiring function 14*a* ends the process without acquiring any magnetic resonance signals.

Of the processing procedure described above, the process at step S101 is realized, for example, as a result of the processing circuitry 16 reading and executing a predetermined program corresponding to the imaging controlling function 16*a* from the storage 12. Further, the processes at steps S102 through S104 and steps S106 through S108 are realized, for example, as a result of the processing circuitry 14 reading and executing a predetermined program corresponding to the acquiring function 14*a* from the storage 12. Also, the processes at steps S105 and S109 are realized, for example, as a result of the processing circuitry 15 reading and executing a predetermined program corresponding to the image generating function 15*a* from the storage 12.

By executing the processing procedure described above, it is possible to perform each of the imaging processes targeting the two nuclides, namely $^1$H and $^{19}$F.

The example was explained above in which the nuclides targeted in the imaging processes are $^1$H and $^{19}$F; however, possible embodiments are not limited to this example. It is also possible to target a nuclide other than $^1$H and $^{19}$F. In those situations, the magnitude of the second static magnetic field shall be set so that, in accordance with the targeted nuclide, the resonance frequency of the nuclide is substantially equal to the resonance frequency of $^1$H in the first static magnetic field.

Further, in the above example, the second static magnetic field is changed to the two magnitudes, namely, zero and the predetermined magnitude corresponding to the nuclide targeted in the imaging process; however, possible embodiments are not limited to this example. It is also acceptable to change the second static magnetic field to zero and a plurality of magnitudes other than zero. With this arrangement, it is possible to perform imaging processes while targeting $^1$H and two or more other nuclides, instead of H and one other nuclide.

As explained above, in the first embodiment, the static magnetic field generator is configured to apply the second static magnetic field in addition to the first static magnetic field serving as a reference. The transmit/receive system is configured to perform the transmitting and receiving at the single frequency. Further, the acquiring function 14*a* is configured to acquire the magnetic resonance signals by employing the transmit/receive system. Further, the transmit/receive system is configured to perform the transmitting and receiving at the resonance frequency of $^1$H in the state in which the first static magnetic field is applied and is configured to perform the transmitting and receiving at the resonance frequency of the nuclide different from $^1$H in the state in which the second static magnetic field is applied in addition to the first static magnetic field.

With these arrangements, it is possible to perform the imaging processes with high image quality, while targeting $^1$H and the nuclide different from $^1$H.

For example, compared to the situations where a dedicated transmit/receive system is provided for each nuclide or where a transmit/receive system is structured to be able to perform transmitting and receiving at multiple resonance frequencies, there is no need to add unnecessary circuitry or elements to the transmit/receive system. Accordingly, it is possible to prevent the image quality from being degraded by electrical noise. Further, for example, there is no need to set the band of the transmit/receive system to a wider band. Accordingly, it is possible to prevent the image quality from being degraded by a larger amount of noise being detected. Further, for example, because there is no need to change the RF coil for each imaging process, there is no need to prepare a dedicated RF coil for each nuclide. Accordingly, even in the situation where an evaluation is made by superimposing an image of another nuclide on an image of $^1$H, it is possible to prevent the image quality of the superimposed images from being degraded due to a positional misalignment between the images.

Compared to the situations where a dedicated transmit/receive system is provided for each nuclide or where a transmit/receive system is structured to be able to perform transmitting and receiving at multiple resonance frequencies, an advantage is also achieved in terms of costs, because it is possible to perform imaging processes with a plurality of nuclides, by using a conventional transmit/receive system targeting $^1$H without any modification.

The embodiment described above may be carried out in various different modes, by modifying a part of the constituent elements of the MRI apparatus 100. Thus, the following will describe some modification examples of the above embodiment as other embodiments.

Second Embodiment

For example, as a second embodiment, the transmit/receive system may be configured to be able to perform transmitting and receiving also at the second frequency tuned to the resonance frequency of a first nuclide different from $^1$H, in addition to the first frequency tuned to the resonance frequency of $^1$H. In that situation, the transmit/receive system is configured to perform transmitting and receiving at one of the first and the second frequencies in the state in which the first static magnetic field is applied and is configured to perform transmitting and receiving in the state in which the resonance frequency of a second nuclide different from both $^1$H and the first nuclide is tuned to the first frequency by the first static magnetic field and the second static magnetic field, in the state in which the second static magnetic field is applied in addition to the first static magnetic field.

Figure 3:
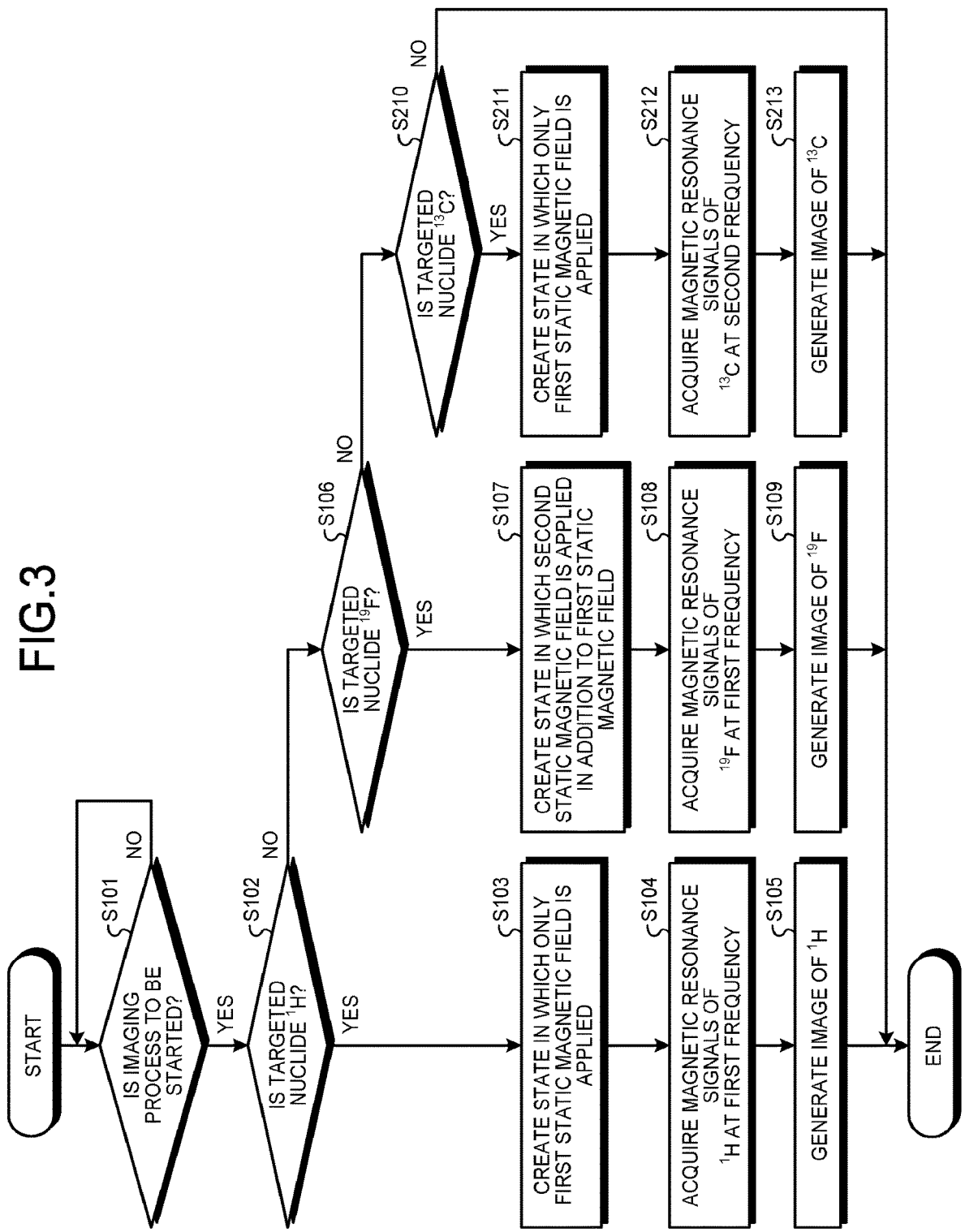
FIG. 3 is a flowchart illustrating a flow in an imaging process performed by an MRI apparatus according to a second embodiment.

FIG. 3 is a flowchart illustrating a flow in an imaging process performed by an MRI apparatus according to the second embodiment.

Similarly to the above example, in the present example, the magnitude of the first static magnetic field is 1.5 T, while the nuclides targeted in the imaging processes are $^1$H and $^{19}$F. It is assumed that the magnitude of the second static magnetic field is set to 0.1 T, while the first frequency is set at 64 MHz. Further, in the present example, the transmit/receive system is configured to be able to perform transmitting and receiving also at the second frequency tuned to the resonance frequency of $^{13}$C, in addition to the first frequency.

For example, as illustrated in FIG. 3, in the present embodiment, the imaging controlling function 16a receives an instruction to start an imaging process from the operator (step S101: Yes). In this situation, for example, the imaging controlling function 16a also receives a designation of a nuclide targeted in the imaging process, as one of the image taking conditions, in addition to receiving the instruction to start the imaging process.

In this situation, because the processes (steps S103 through S105) performed when the targeted nuclide is $^1$H (step S102: Yes) and the processes (steps S107 through S109) performed when the targeted nuclide is $^{19}$F (step S102: No; and step S106: Yes) are the same as the processes at steps S103 through S105 and the processes at steps S107 through S109 illustrated in FIG. 2, respectively, the explanations thereof will be omitted.

After that, in the present embodiment, when the targeted nuclide designated by the operator is neither $^1$H nor $^{19}$F (step S102: No; and step S106: No), but is $^{13}$C (step S210: Yes), the acquiring function 14a creates a state in which only the first static magnetic field is applied, by controlling the static magnetic field power source 18 so as not to supply an electric current to the second static magnetic field magnet (step S211).

Subsequently, the acquiring function 14a acquires magnetic resonance signals of $^{13}$C, by controlling the transmit/receive system so as to perform transmitting and receiving at the second frequency (step S212). Further, the image generating function 15a generates an image of $^{13}$C, on the basis of the acquired magnetic resonance signals (step S213).

In contrast, when the targeted nuclide designated by the operator is none of $^1$H, $^{19}$F, and $^{13}$C (step S102: No, step S106: No; and step S210: No), the acquiring function 14a ends the process without acquiring any magnetic resonance signals.

Of the processing procedure described above, the process at step S101 is realized, for example, as a result of the processing circuitry 16 reading and executing the predetermined program corresponding to the imaging controlling function 16a from the storage 12. Further, the processes at steps S102 through S104, steps S106 through S108, and steps S210 through S213 are realized, for example, as a result of the processing circuitry 14 reading and executing the predetermined program corresponding to the acquiring function 14a from the storage 12. Also, the processes at steps S105, S109, and S213 are realized, for example, as a result of the processing circuitry 15 reading and executing the predetermined program corresponding to the image generating function 15a from the storage 12.

By executing the processing procedure described above, it is possible to perform each of the imaging processes targeting the three nuclides, namely $^1$H, $^{19}$F, and $^{13}$C.

The example was explained above in which the second frequency is tuned to the resonance frequency of $^{13}$C; however, possible embodiments are not limited to this example. For instance, the second frequency may be tuned to the resonance frequency of a nuclide other than $^{13}$C.

Further, another arrangement is also acceptable in which the transmit/receive system is configured to acquire magnetic resonance signals of yet another nuclide, by performing transmitting and receiving at the second frequency, in the state in which the second static magnetic field is applied in addition to the first static magnetic field. In that situation, it is possible to perform an imaging process targeting the abovementioned other nuclide, in addition to a certain set of three nuclides including $^1$H.

With the arrangements described above, it is possible to perform the imaging processes with high image quality, while targeting three or more nuclides including $^1$H.

Third Embodiment

Further, for example, as a third embodiment, the acquiring function 14a may be configured to perform an imaging process targeting $^1$H and an imaging process targeting a nuclide different from $^1$H, by implementing an image taking method by which magnetic resonance signals used for generating images are acquired in multiple separate sessions at intervals called Repetition Time (TR). In that situation, the data acquisitions to acquire the magnetic resonance signals of $^1$H while the first static magnetic field is applied and the data acquisitions to acquire the magnetic resonance signals of the nuclide different from $^1$H while the second static magnetic field is applied in addition to the first static magnetic field may be performed alternately in correspondence with the TR.

For example, when the nuclides targeted in the imaging processes are $^1$H and $^{19}$F as described in the first embodiment, the acquiring function 14a is configured to alternately perform, in correspondence with the TR, the data acquisitions to acquire the magnetic resonance signals of $^1$H and the data acquisitions to acquire the magnetic resonance signals of $^{19}$F. Further, for example, when the nuclides targeted in the imaging processes are $^1$H, $^{19}$F, and $^{13}$C as described in the second embodiment, the acquiring function 14a is configured to sequentially perform, in correspondence with the TR, the data acquisitions to acquire the magnetic resonance signals of $^1$H, the data acquisitions to acquire the magnetic resonance signals of $^{19}$F, and the data acquisitions to acquire the magnetic resonance signals of $^{13}$C.

With the arrangements described above, it is possible to perform the imaging processes targeting $^1$H and the imaging processes targeting the one or more other nuclides in mutually the same temporal phase. Accordingly, in the situations where an evaluation is made by superimposing an image of the other nuclide on an image of $^1$H, it is possible to keep positional misalignments small between the images. It is therefore possible to improve the image quality of the superimposed images.

Fourth Embodiment

Further, for example, as a fourth embodiment, in the imaging process targeting a nuclide different from $^1$H, the acquiring function 14a may be configured to acquire magnetic resonance signals with respect to a range in the k-space smaller than that in the imaging process targeting $^1$H.

For example, in the imaging process targeting the nuclide different from $^1$H, the acquiring function 14a may be configured to acquire the magnetic resonance signals with respect to a region in a central part of the k-space that has many low frequency components.

With this arrangement, when the imaging process is performed while targeting the nuclide different from $^1$H, it is possible to reduce the amount of magnetic resonance signals to be acquired. It is therefore possible to shorten the image taking period.

Fifth Embodiment

Further, for example, as a fifth embodiment, the static magnetic field generator may be realized by using a static magnetic field magnet capable of generating the first static magnetic field and a static magnetic field having a magnitude equal to a result of adding the second static magnetic field to the first static magnetic field.

Figure 4:
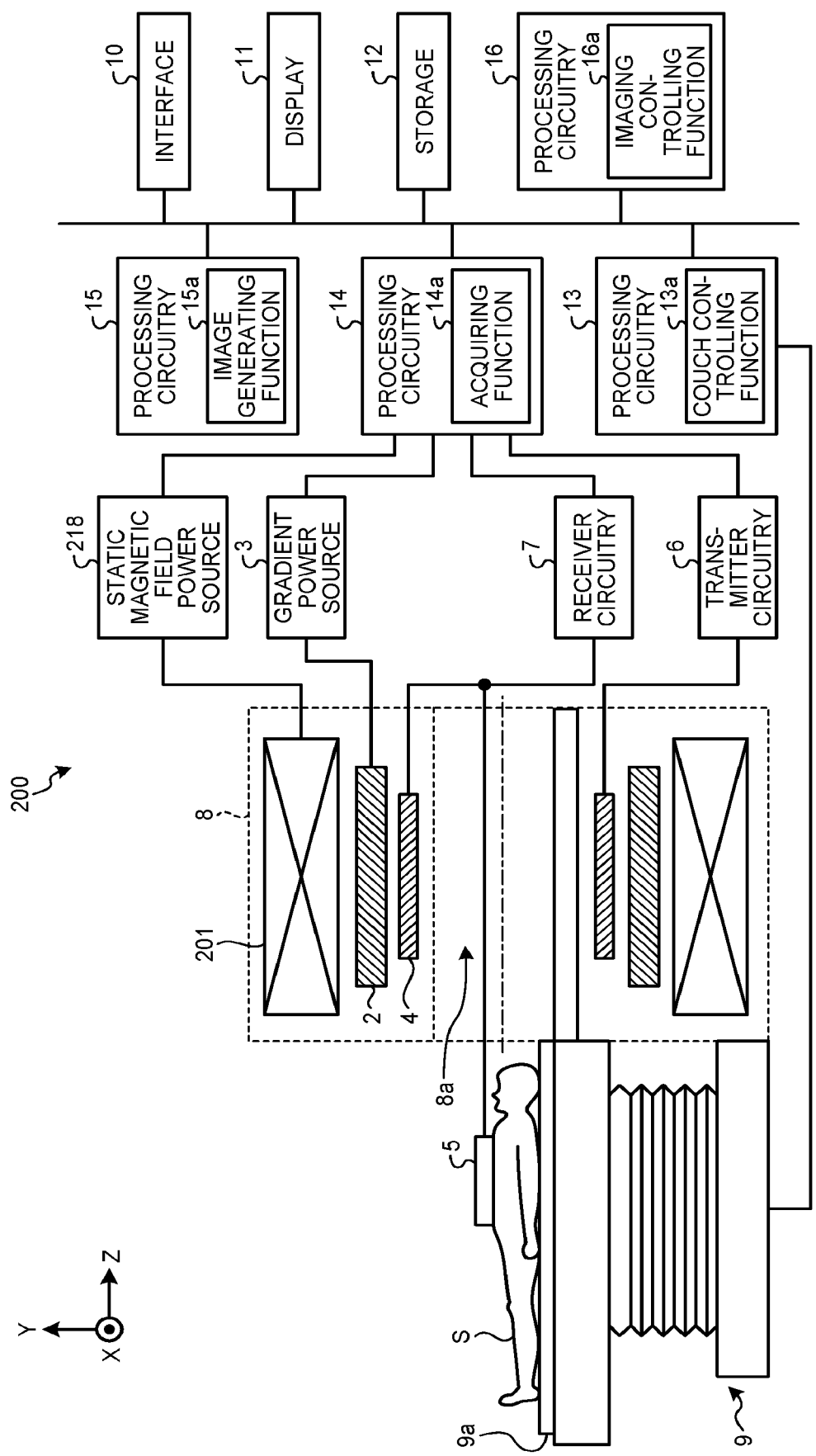
FIG. 4 is a diagram illustrating an exemplary configuration of an MRI apparatus according to a fifth embodiment.

FIG. 4 is a diagram illustrating an exemplary configuration of an MRI apparatus according to the fifth embodiment.

For example, as illustrated in FIG. 4, an MRI apparatus 200 according to the present embodiment includes a static magnetic field magnet 201, a static magnetic field power source 218, the gradient coil 2, the gradient power source 3, the whole body Radio Frequency (RF) coil 4, the local RF coil 5, the transmitter circuitry 6, the receiver circuitry 7, the gantry 8, the couch 9, the interface 10, the display 11, the storage 12, and the pieces of processing circuitry 13 to 16.

In the present example, the constituent elements other than the static magnetic field magnet 201, the static magnetic field power source 218, and the acquiring function 14a are the same as those in the first embodiment.

Further, in the present embodiment, a static magnetic field generator is realized by the static magnetic field magnet 201 and the static magnetic field power source 218.

The static magnetic field magnet 201 is configured to generate a static magnetic field in an image taking space in which the subject S is placed. More specifically, the static magnetic field magnet 201 is formed to have a hollow and substantially circular cylindrical shape (which may have an oval cross-section orthogonal to the central axis thereof) and is configured to generate a static magnetic field in the image taking space formed on the inner circumferential side thereof. In the present embodiment, the static magnetic field magnet 201 is an electromagnet realized by using a coil formed to have a hollow and substantially circular cylindrical shape and is configured to generate a static magnetic field having any of various magnitudes in accordance with the magnitude of the electric current supplied thereto from the static magnetic field power source 218.

Under the control of the acquiring function 14a, the static magnetic field power source 218 is configured to supply the static magnetic field magnet 201 with the electric current used for causing the static magnetic field magnet 201 to generate the static magnetic field.

Further, in the present embodiment, when $^1$H is targeted in an imaging process, the acquiring function 14a is configured to create a state in which only the first static magnetic field is applied, by controlling the static magnetic field power source 218. In contrast, when a nuclide different from $^1$H is targeted in an imaging process, the acquiring function 14a is configured to create a state in which the static magnetic field having the magnitude equal to the result of adding the second static magnetic field to the first static magnetic field is applied, by controlling the static magnetic field power source 218.

Further, similarly to the first embodiment, the acquiring function 14a is configured to control the transmit/receive system in accordance with the nuclide targeted in the imaging processes. As a result of this control, the transmit/receive system performs transmitting and receiving at the first frequency tuned to the resonance frequency of $^1$H. Further, the transmit/receive system is configured to perform transmit/receive at the first frequency in the state in which the first static magnetic field is applied and is configured to perform transmitting and receiving in the state in which the resonance frequency of the nuclide different from $^1$H is tuned to the first frequency by the first static magnetic field and the second static magnetic field, in the state in which the second static magnetic field is applied in addition to the first static magnetic field.

With these arrangements, similarly to the first embodiment, it is possible to perform the imaging processes with high image quality while targeting $^1$H and the nuclide different from $^1$H.

In the embodiments above, the example is explained in which the MRI apparatus has a so-called tunnel-like structure in which the static magnetic field magnet, the gradient coil, and the whole body RF coil are each formed to have a substantially circular cylindrical shape; however, possible embodiments are not limited to this example. For instance, the MRI apparatus may have a so-called open structure in which a pair of static magnetic field magnets, a pair of gradient coils, and a pair of RF coils are arranged so as to oppose each other while the image taking space in which the subject is placed is interposed therebetween. In the open structure, the space interposed between the pair of static magnetic field magnets, the pair of gradient coils, and the pair of RF coils corresponds to the bore in the tunnel-like structure.

Further, each of the embodiments described above may be carried out alone or may be carried out as being combined, as appropriate, with one or more other embodiments.

Further, in the embodiments above, the example was explained in which the acquiring means of the present disclosure is realized by the acquiring function 14a included in the processing circuitry 14; however, possible embodiments are not limited to this example. For instance, instead of being realized by the acquiring function 14a described in the embodiments, the functions of the acquiring means of the present disclosure may be realized by using only hardware, by using only software, or by using a combination of hardware and software.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in a storage. Alternatively, instead of saving the programs in the storage, it is also acceptable to directly incorporate the programs in the circuits of the one or more processors. In that situation, the one or more processors realize the functions by reading and executing the programs incorporated in the circuits thereof. Further, the one or more processors of the present embodiments do not each necessarily have to be structured as a single circuit. It is also acceptable to structure one processor by combining together a plurality of independent circuits so as to realize the functions thereof.

In this regard, the programs executed by the one or more processors are provided as being incorporated, in advance, in a Read Only Memory (ROM), a storage, or the like. The programs may be provided as being recorded in a computer-readable storage medium such as a Compact Disk Read-Only Memory (CD-ROM), a Flexible Disk (FD), a Compact Disk Recordable (CD-R), Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the functional units described above. In the actual hardware, as a result of a CPU reading and executing the programs from a storage medium such as a ROM, the modules are loaded into a main storage device and generated in the main storage device.

According to at least one aspect of the embodiments described above, it is possible to perform the imaging processes with high image quality while targeting the hydrogen nuclei $^1$H and the nuclide different from $^1$H.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a first static magnetic field magnet configured to apply to a first static magnetic field serving as a reference;
a second static magnetic field magnet configured to apply a second static magnetic field in addition to the first static magnetic field;
a transmit/receive system configured to perform transmitting and receiving at a single frequency; and
processing circuitry configured to acquire a magnetic resonance signal by employing the transmit/receive system, wherein
the transmit/receive system is configured to perform transmitting and receiving at a resonance frequency of a hydrogen nucleus in a state in which the first static magnetic field is applied and is configured to perform transmitting and receiving at a resonance frequency of a nuclide different from the hydrogen nucleus in a state in which the second static magnetic field is applied in addition to the first static magnetic field.

2. The magnetic resonance imaging apparatus according to claim 1, wherein
the transmit/receive system is configured to perform the transmitting and receiving by using, as the single frequency, a first frequency tuned to the resonance frequency of the hydrogen nucleus,
in the state in which the first static magnetic field is applied, the transmit/receive system is configured to perform the transmitting and receiving at the first frequency, and
in the state in which the second static magnetic field is applied in addition to the first static magnetic field, the transmit/receive system is configured to perform the transmitting and receiving in a state in which the resonance frequency of the nuclide different from the hydrogen nucleus is tuned to the first frequency by the first static magnetic field and the second static magnetic field.

3. The magnetic resonance imaging apparatus according to claim 2, wherein
in addition to the first frequency, the transmit/receive system is configured to be able to perform transmitting and receiving also at a second frequency tuned to a resonance frequency of a first nuclide different from the hydrogen nucleus,
in the state in which the first static magnetic field is applied, the transmit/receive system is configured to perform transmitting and receiving at one of the first and the second frequencies, and
in the state in which the second static magnetic field is applied in addition to the first static magnetic field, the transmit/receive system is configured to perform the transmitting and receiving in a state in which a resonance frequency of a second nuclide different from both the hydrogen nucleus and the first nuclide is tuned to the first frequency by the first static magnetic field and the second static magnetic field.

4. The magnetic resonance imaging apparatus according to claim 2, wherein the state in which the resonance frequency of the nuclide different from the hydrogen nucleus is tuned to the first frequency is a state in which the resonance frequency of the nuclide is tuned so as to be included in a band of the transmit/receive system and a band of an image.

5. The magnetic resonance imaging apparatus according to claim 2, wherein, when the nuclide different from the hydrogen nucleus is a nuclide of which a spin rotation direction is opposite to that of the hydrogen nucleus, the transmit/receive system tunes the resonance frequency of the nuclide different from the hydrogen nucleus to the first frequency, by inverting a phase of a radio frequency used in the transmitting and receiving in the state in which the second static magnetic field is applied in addition to the first static magnetic field.

6. The magnetic resonance imaging apparatus according to claim 1, wherein, in the state in which the second static magnetic field is applied in addition to the first static magnetic field, the transmit/receive system sets a receive gain of a magnetic resonance signal of the nuclide different from the hydrogen nucleus to be larger than a receive gain of a magnetic resonance signal of the hydrogen nucleus.

7. The magnetic resonance imaging apparatus according to claim 1, wherein, when an imaging process targeting the hydrogen nucleus and an imaging process targeting the nuclide different from the hydrogen nucleus are performed by implementing an image taking method by which magnetic resonance signals used for generating an image are acquired in multiple separate sessions at intervals called repetition time, the processing circuitry alternately performs, in correspondence with the repetition time, data acquisitions to acquire a magnetic resonance signal of the hydrogen nucleus while the first static magnetic field is applied and data acquisitions to acquire a magnetic resonance signal of the nuclide different from the hydrogen nucleus while the second static magnetic field is applied in addition to the first static magnetic field.

8. The magnetic resonance imaging apparatus according to claim 7, wherein, in the imaging process targeting the nuclide different from the hydrogen nucleus, the processing circuitry acquires the magnetic resonance signal with respect to a range in a k-space smaller than that in the imaging process targeting the hydrogen nucleus.

9. A magnetic resonance imaging apparatus comprising:
a static magnetic field generator configured to apply a second static magnetic field in addition to a first static magnetic field serving as a reference;

a transmit/receive system configured to perform transmitting and receiving at a single frequency; and processing circuitry configured to acquire a magnetic resonance signal by employing the transmit/receive system, wherein the transmit/receive system is configured to perform transmitting and receiving at a resonance frequency of a hydrogen nucleus in a state in which the first static magnetic field is applied and is configured to perform transmitting and receiving at a resonance frequency of a nuclide different from the hydrogen nucleus in a state in which the second static magnetic field is applied in addition to the first static magnetic field, and, when an imaging process targeting the hydrogen nucleus and an imaging process targeting the nuclide different from the hydrogen nucleus are performed by implementing an image taking method by which magnetic resonance signals used for generating an image are acquired in multiple separate sessions at intervals called repetition time, the processing circuitry alternately performs, in correspondence with the repetition time, data acquisitions to acquire a magnetic resonance signal of the hydrogen nucleus while the first static magnetic field is applied and data acquisitions to acquire a magnetic resonance signal of the nuclide different from the hydrogen nucleus while the second static magnetic field is applied in addition to the first static magnetic field, wherein, in the imaging process targeting the nuclide different from the hydrogen nucleus, the processing circuitry acquires the magnetic resonance signal with respect to a range in a k-space smaller than that in the imaging process targeting the hydrogen nucleus.

* * * * *